United States Patent
Yang et al.

(10) Patent No.: US 8,663,598 B2
(45) Date of Patent: Mar. 4, 2014

(54) ANTI-HUMAN TRANSFERRIN RECEPTOR ANTIBODY AND USES THEREOF

(75) Inventors: Ming-Hua Yang, Taipei (TW); Min-Yuan Chou, Taipei (TW); Hsiang-Ching Wang, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 13/610,583

(22) Filed: Sep. 11, 2012

(65) Prior Publication Data

US 2013/0171061 A1 Jul. 4, 2013

(30) Foreign Application Priority Data

Dec. 29, 2011 (TW) .............................. 100149460 A (51) Int. Cl.
| | |
|---|---|
| A61K 51/00 | (2006.01) |
| A61M 36/14 | (2006.01) |
| A61B 5/055 | (2006.01) |
| A61K 49/04 | (2006.01) |
| A61B 5/00 | (2006.01) |
| A61B 8/00 | (2006.01) |
| A61B 10/00 | (2006.01) |
| G01N 33/567 | (2006.01) |
| G01N 33/574 | (2006.01) |
| C12P 21/08 | (2006.01) |
| C07K 16/00 | (2006.01) |

(52) U.S. Cl.
USPC ............ 424/1.49; 424/9.34; 424/9.4; 424/9.6; 435/7.21; 435/7.23; 530/387.3; 530/389.1; 530/389.3

(58) Field of Classification Search
None
See application file for complete search history.

(56) References Cited

U.S. PATENT DOCUMENTS

| | | | |
|---|---|---|---|
| 5,648,469 | A | 7/1997 | Trowbridge et al. |
| 5,762,932 | A | 6/1998 | Kemp |
| 5,977,307 | A | 11/1999 | Friden et al. |
| 6,015,555 | A | 1/2000 | Friden |
| 6,329,508 | B1 | 12/2001 | Friden |
| 7,572,895 | B2 | 8/2009 | Mather et al. |
| 7,943,129 | B2 | 5/2011 | Muruganandam et al. |
| 7,976,841 | B2 | 7/2011 | Monteiro et al. |
| 7,981,417 | B2 | 7/2011 | Shusta et al. |
| 2010/0166745 | A1 | 7/2010 | Mather et al. |

OTHER PUBLICATIONS

Paul WE. Fundamental Immunology. 3rd ed. Raven Press, NY. p. 292-295 (1993).*
Rudikoff S et al. PNAS. 79:1979-1983 (Mar. 1982).*
Coleman PM. Research in Immunology. 145(1):33-36 (Jan. 1994).*
Pirollo, et al., "A Tumor-Targeted Nanodelivery System to Improve Early MRI Detection of Cancer", Molecular Imaging, vol. 5, No. 1, Jan. 2006, pp. 41-52.
Freedman, et al., "Nanodelivery of MRI Contrast Agent Enhances Sensitivity of Detection of Lung Cancer Metastases", Acad. Radiol. May 2009, 16(5), pp. 627-637.
Daniels, et al., "Conjugation of an anti-transferrin receptor IgG3-avidin fusion protein with biotinylated saporin results in significant enhancement of its cytotoxicity against malignant hematopoietic cells", Mol. Cancer Ther. 2007; pp. 6:2995-6:3008.
Callens, et al., "Recent advances in adult T-cell leukemia therapy: focus on a new anti-transferrin receptor monoclonal antibody", Leukemia, 2008, 22, pp. 42-48.
Moura, et al., "A neutralizing monoclonal antibody (mAb A24) directed against the transferrin receptor induces apoptosis of tumor T lymphocytes from ATL patients", Blood, Industrial Tech. Res. Inst., 2011, pp. 1838-1845.
Gosk, et al., "Targeting Anti-Transferrin Receptor Antibody (OX26) and OX26-Conjugated Liposomes to Brain Capillary Endothelial Cells Using In Situ Perfusion", Journal of Cerebral Blood Flow & Metabolism 24, 2004, pp. 1193-1204.
Shen, et al., "An anti-transferrin receptor antibody enhanced the growth inhibitory effects of chemotherapeutic drugs on human non-hematopoietic tumor cells", International Immunopharmacology, 8, 2008, pp. 1813-1820.
Crepin, et al., "Development of Human Single-Chain Antibodies to the Transferrin Receptor that Effectively Antagonize the Growth of Leukemias and Lymphomas", Cancer Research, 2010, pp. 5497-5506.
Lee, et al., "Selection of human antibody fragments by phage display", Nature Protocols, vol. 2, No. 11, 2007, pp. 3001-3008.
Jones, et al., "Effects of Transferrin Receptor Blockade on Cancer Cell Proliferation and Hypoxia-Inducible Factor Function and Their Differential Regulation by Ascorbate", Cancer Research, 2006, pp. 2749-2756.
Shen, et al., "Engineering and characterization of a baculovirus-expressed mouse/human chimeric antibody against transferrin receptor", Protein Engineering Design & Selection, vol. 22, No. 12, 2009, pp. 723-731.
Xu, et al., "An anti-transferrin receptor antibody enhanced the growth inhibitory effects of chemotherapeutic drugs on human glioma cell", International Immunopharmacology, 2011, pp. 1-7.
Dao-Feng Yang, et al., "Construction of single chain Fv antibody against transferrin receptor and its protein fusion with alkaline phosphatase", World Journal of Gastroenterology, 2005, vol. 11, No. 21, pp. 3300-3303.
Taiwanese Office Action dated Nov. 27, 2013, as issued in corresponding Taiwan Patent Application No. 10221633850.

* cited by examiner

*Primary Examiner* — Robert Landsman
(74) *Attorney, Agent, or Firm* — Muncy, Geissler, Olds & Lowe, PLLC (57) ABSTRACT

One embodiment of the disclosure provides an amino sequence of an anti-human transferrin receptor antibody, including: an amino sequence of a heavy chain variable region which is represented by SEQ ID NO.: 1 or SEQ ID NO.: 2, wherein the anti-human transferrin receptor antibody is capable of specifically binding to a human transferrin receptor.

18 Claims, 5 Drawing Sheets

```
                        SEQUENCE LISTING

<160> NUMBER OF SEQ ID NOS: 5

<210> SEQ ID NO 1
<211> LENGTH: 121
<212> TYPE: PRT
<213> ORGANISM: Homo sapiens

<400> SEQUENCE: 1

Met Ala Gln Val Gln Leu Leu Glu Ser Gly Gly Gly Leu Val Gln Pro
1               5                   10                  15

Gly Gly Ser Leu Arg Leu Ser Cys Ala Ala Ser Gly Phe Ile Phe Asn
            20                  25                  30

Thr Glu Tyr Met Ala Trp Val Arg Gln Ala Pro Gly Lys Gly Leu Glu
        35                  40                  45

Trp Val Ser Ala Ile Lys Glu Gln Ser Gly Ser Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Ala Gln Met His His Glu Ala Glu Val Lys Phe Trp Gly
            100                 105                 110

Gln Gly Thr Leu Val Thr Val Ser Ser
        115                 120

<210> SEQ ID NO 2
<211> LENGTH: 127
<212> TYPE: PRT
<213> ORGANISM: Homo sapiens

<400> SEQUENCE: 2
```

```
Met Ala Gln Val Gln Leu Leu Glu Ser Gly Gly Gly Leu Val Gln Pro
1               5                   10                  15

Gly Gly Ser Leu Arg Leu Ser Cys Ala Ala Ser Gly Phe Lys Phe Ser
            20                  25                  30

Ala Glu Tyr Met Ser Trp Val Arg Gln Ala Pro Gly Lys Gly Leu Glu
        35                  40                  45

Trp Val Ser Thr Ile Lys Met Asn Asn Gly Ser Thr Tyr Tyr Ala Asp
    50                  55                  60

Ser Val Lys Gly Arg Phe Thr Ile Ser Arg Asp Asn Ser Lys His Thr
65                  70                  75                  80

Leu Tyr Leu Gln Met Asn Ser Leu Arg Ala Glu Asp Thr Ala Val Tyr
                85                  90                  95

Tyr Cys Ala Arg Pro Met Ala Trp Arg Gly Asn Val Val Arg Ala Glu
            100                 105                 110

Asn Leu Arg Phe Trp Gly Gln Gly Thr Leu Val Thr Val Ser Ser
            115                 120                 125
```

<210> SEQ ID NO 3
<211> LENGTH: 363
<212> TYPE: DNA
<213> ORGANISM: Homo sapiens

<400> SEQUENCE: 3

```
atggcccagg tgcagctgtt ggagtctggg ggaggcttgg tacagcctgg ggggtccctg      60
cgtctctcct gtgcagcctc cggatttatc tttaacactg agtatatggc ctgggtccgc     120
caggctccag ggaagggtct agagtgggta tcagccatta aggagcaaag cggtagcaca     180
tactacgcag actccgtgaa gggccggttc accatctccc gtgacaattc caagaacacg     240
ctgtatctgc aaatgaacag cctgcgtgcc gaggacaccg cggtatatta ttgcgcggct     300
cagatgcatc atgaggccga ggtcaagttt tggggtcagg gaaccctggt caccgtctcg     360
agc                                                                    363
```

<210> SEQ ID NO 4
<211> LENGTH: 381
<212> TYPE: DNA
<213> ORGANISM: Homo sapiens

<400> SEQUENCE: 4

```
atggcccagg tgcagctgtt ggagtctggg ggaggcttgg tacagcctgg ggggtccctg      60
cgtctctcct gtgcagcctc cggatttaag tttagcgctg agtatatgag ctgggtccgc     120
caggctccag ggaagggtct agagtgggta tcaaccatta agatgaataa cggtagcaca     180
tactacgcag actccgtgaa gggccggttc accatctccc gtgacaattc caagcacacg     240
ctgtatctgc aaatgaacag cctgcgtgcc gaggacaccg cggtatatta ttgcgcgaga     300
ccgatggcgt ggcggggtaa tgtggtgcgg gccgagaact gcggttttg gggtcaggga      360 accctggtca ccgtctcgag c                                               381
```

<210> SEQ ID NO 5
<211> LENGTH: 17
<212> TYPE: DNA
<213> ORGANISM: Artificial
<220> FEATURE:
<223> OTHER INFORMATION: Primer

<400> SEQUENCE: 5

```
caggaaacag ctatgac                                                     17
```

ANTI-HUMAN TRANSFERRIN RECEPTOR ANTIBODY AND USES THEREOF

CROSS REFERENCE TO RELATED APPLICATIONS

This Application claims priority of Taiwan Patent Application No. 100149460, filed on Dec. 29, 2011, the entirety of which is incorporated by reference herein.

INCORPORATION BY REFERENCE OF SEQUENCE LISTING

A sequence listing submitted as a text file via EFS-Web is incorporated herein by reference. The text file containing the sequence listing is named "0965-A23835-US_Seq_Listing.txt"; its date of creation is Jul. 3, 2012; and its size is 3,931 bytes.

TECHNICAL FIELD

The technical field relates to an anti-human transferrin receptor antibody and uses thereof.

BACKGROUND

The transferrin receptor (TfR) (also known as CD71), a type II transmembrane glycoprotein made of two 90-kDa monomers on the surface of cells, is a vital protein which is involved in iron homeostasis and the regulation of cell growth (reviewed in Daniels T R et al., Clin Immunol. 121(2):144-58, 2006). The expression amount of transferrin receptor is significantly upregulated in highly proliferating cells, and the increased expressions for the transferrin receptors at each cancer stage have differences, and differences in the expression amounts can help to avoid incorrect determinations of the cancer stage (Shindelman J E et al., Int J Cancer. 27:329-34, 1981; Sciot R et al., Histopathology. 16:59-62, 1990; Le N T et al., Biochim Biophys Acta 1603:31-46, 2002). Since transferrin receptors are strongly expressed by most malignant cells, are present on cell surfaces, and have the properties of being bound and detected easily and mediated by endocytosis, they have long been considered an effective target for targeted cancer therapies.

A number of anti-transferrin receptor monoclonal antibodies have been demonstrated to inhibit the growth of many cell types. For example, the murine monoclonal anti-human transferrin receptor antibody 42/6, the first to use an anti-transferrin receptor antibody in a clinical trial, is confirmed to be able to inhibit malignant cell growth (Brooks D et al., Clin Cancer Res. 1(11):1259-65, 1995). In addition, by transferrin receptor-mediated endocytosis, therapeutic agents can be delivered to tumor cells through transferrin receptors. Moreover, the high expression level of transferrin receptor is also found on the blood brain barrier, which makes of interest for therapeutic or diagnostic approaches in brain diseases. For instance, the anti-transferrin receptor antibody OX-26 could be used as a carrier for the delivery of drugs across the blood-brain barrier (Friden P M et al. Proc Natl Acad Sci U S A. 88(11):4771-5, 1991).

The use of monoclonal antibodies in the clinical treatment of cancer started in the early 1980s. Unfortunately, murine monoclonal antibodies have been far from ideal in the treatment of humans. Due to the short half-life of the murine monoclonal antibodies in human bodies, the murine monoclonal antibodies require frequent administration to maintain therapeutic levels (Manuel L. Penichetn and Sherie L. Morrison, Drug Dev. Res. 61:121-136, 2004). In addition, patients treated with these murine antibodies often produce human anti-mouse antibodies (HAMA) that neutralizes the murine monoclonal antibodies, decreases the half-life of the murine monoclonal antibodies, and in some cases was associated with severe allergic reactions (Abramowicz D et al., N Engl. J. Med. 327:736, 1992).

SUMMARY

One embodiment of the disclosure provides an amino sequence of an anti-human transferrin receptor antibody, comprising: an amino sequence of a heavy chain variable region represented by SEQ ID NO.: 1 or SEQ ID NO.: 2, wherein the anti-human transferrin receptor antibody is capable of specifically binding to a human transferrin receptor.

One embodiment of the disclosure also provides an anti-human transferrin receptor antibody, comprising: a heavy chain variable region having an amino sequence represented by SEQ ID NO.: 1 or SEQ ID NO.: 2, wherein the anti-human transferrin receptor antibody is capable of specifically binding to a human transferrin receptor.

One embodiment of the disclosure further provides a fusion protein, comprising: the anti-human transferrin receptor antibody as mentioned above; and a fragment crystallizable region (Fc) of a human immunoglobulin G connected to the anti-human transferrin receptor antibody, wherein the fusion protein is capable of specifically binding to a human transferrin receptor.

One embodiment of the disclosure further provides an imaging agent, comprising: the anti-human transferrin receptor antibody as mentioned above; and a labeling material connected to the anti-human transferrin receptor antibody.

One embodiment of the disclosure further provides a method for labeling or imaging a cell or tissue, comprising: providing an imaging agent, wherein the imaging agent comprises the anti-human transferrin receptor antibody as mentioned above and a labeling material connected to the anti-human transferrin receptor antibody; and contacting the imaging agent with a cell or tissue to be labeled or imaged, wherein the antibody of the imaging agent binds to a human transferrin receptor expressed by the cell or tissue and causes the cell or tissue be labeled or imaged.

One embodiment of the disclosure provides a pharmaceutical composition, comprising: an effective amount of an antibody comprising a heavy chain variable region, wherein an amino sequence of the heavy chain variable region comprises a sequence represented by SEQ ID NO.: 1 or SEQ ID NO.: 2, and the antibody is capable of specifically binding to a human transferrin receptor.

A detailed description is given in the following embodiments with reference to the accompanying drawings.

BRIEF DESCRIPTION OF THE DRAWINGS

The embodiments of disclosure can be more fully understood by reading the subsequent detailed description and examples with references made to the accompanying drawings, wherein.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

In one embodiment of the present disclosure, the present disclosure provides an amino sequence of an antibody which is capable of specifically binding to a human transferrin receptor. The above-mentioned antibody comprises a single heavy chain variable region, which is able to be used as a single domain antibody (sdAb).

The amino sequence of the antibody of the disclosure may comprise an amino sequence of a heavy chain variable region represented by SEQ ID NO.: 1 or SEQ ID NO.: 2. In one embodiment, the amino sequence of the antibody of the disclosure may be obtained through a phage display selection which comprises the following steps but is not limited thereto.

First, a human domain antibody library is provided, and the human domain antibody library is an antibody library which is composed of segments of heavy chain variable region antibody.

Next, by using a phage display technique, a selection is performed to the antibody library with a human transferrin receptor to select a phage which is able to express an antibody capable of binding to the human transferrin receptor.

Then, a nucleotide sequencing is performed on the selected phage mentioned above to obtain a nucleotide sequence of the antibody expressed by the selected phage.

Finally, according to the nucleotide sequence of the antibody mentioned above, the amino sequence of the antibody which is capable of binding to a human transferrin receptor of the disclosure may be predicted.

In one embodiment, the nucleotide sequence of the antibody obtained by nucleotide sequencing of the selected phage mentioned above is a nucleotide sequence represented by SEQ ID NO.: 3, and the foregoing amino sequence represented by SEQ ID NO.: 1 may be encoded by the nucleotide sequence represented by SEQ ID NO.: 3.

In another embodiment, the nucleotide sequence of the antibody obtained by nucleotide sequencing of the selected phage mentioned above is a nucleotide sequence represented by SEQ ID NO.: 4, and the foregoing amino sequence represented by SEQ ID NO.: 2 may be encoded by the nucleotide sequence represented by SEQ ID NO.: 4.

"Phage display selection" mentioned herein is a technique which is the same as the technique of phage display selection well known in the art. Simply, the method for selection of the present disclosure inserts a demand DNA fragment into a gene region for coat protein to make a protein (polypeptide) encoded by the demand DNA fragment to be expressed on the surface of the phage to select the demand protein (polypeptide). Since the method for selecting the antibody of the present disclosure is based on phage display selection, various variations due to the traditional technique of adopting animal immunization may be avoided.

In one embodiment, by binding to a human transferrin receptor expressed on a cell, the foregoing antibody of the present disclosure is capable of entering the cell through receptor-mediated endocytosis.

Furthermore, the amino acid sequence of the antibody of the present disclosure mentioned above may be a human sequence.

In another embodiment of the present disclosure, according to the amino acid sequence of the antibody of the present disclosure mentioned above, the present disclosure may provide an antibody which is capable of specifically binding to a human transferrin receptor.

In one embodiment, the above-mentioned antibody of the present disclosure may comprise a heavy chain variable region having an amino sequence represented by SEQ ID NO.: 1 or SEQ ID NO.: 2.

In addition, by binding to a human transferrin receptor expressed on a cell, the above-mentioned antibody of the present disclosure is capable of entering the cell through receptor-mediated endocytosis.

The amino acid sequence of the antibody of the present disclosure mentioned above may be a human sequence. Since the amino acid sequence of the antibody of the present disclosure may be a human sequence, the problem resulting in human anti-mouse antibodies (HAMA) during the application of the antibody of the disclosure may be prevented.

In a further embodiment of the present disclosure, the present disclosure may provide a fusion protein which is capable of specifically binding to a human transferrin receptor. The above-mentioned fusion protein may comprise the antibody of the present disclosure and a fragment crystallizable region (Fc) of a human immunoglobulin G connected to the anti-human transferrin receptor antibody, and the above-mentioned fusion protein is in a form of $V_H$-Fc.

In the fusion protein, the antibody of the present disclosure may comprise a heavy chain variable region having an amino sequence represented by SEQ ID NO.: 1 or SEQ ID NO.: 2, and the foregoing fragment crystallizable region (Fc) of a human immunoglobulin G may comprise a fragment crystallizable region (Fc) of a human immunoglobulin G1 (IgG1), immunoglobulin G2 (IgG2), immunoglobulin G3 (IgG3) or immunoglobulin G4 (IgG4). In one embodiment, the fragment crystallizable region (Fc) of a human immunoglobulin G is a fragment crystallizable region (Fc) of a human immunoglobulin G1 (IgG1).

In one embodiment, by fusing the amino sequence of the antibody of the disclosure with an amino sequence of the fragment crystallizable region (Fc) of the human immunoglobulin G, the above-mentioned fusion protein may be obtained. In one embodiment, the amino sequence of the fragment crystallizable region (Fc) of a human immunoglobulin G is an amino sequence of a fragment crystallizable region (Fc) of a human immunoglobulin G1 (IgG1) that is able to be obtained from GenBank Accession number AAD38158.

In another embodiment, through a recombinant DNA technique, the above-mentioned fusion protein may be obtained by connecting the nucleotide sequence encoding the amino sequence of the antibody of the present disclosure to the nucleotide sequence encoding the fragment crystallizable region (Fc) of the human immunoglobulin G to form a recombinant nucleotide sequence, and then expressing the recombinant nucleotide sequence. The nucleotide sequence encoding the amino sequence of the antibody of the present disclosure may comprise a nucleotide sequence represented by SEQ ID NO.: 3 or SEQ ID NO.: 4. The nucleotide sequence encoding the fragment crystallizable region (Fc) of the human immunoglobulin G may comprise a nucleotide sequence encoding a fragment crystallizable region (Fc) of a human immunoglobulin G1 (IgG1), immunoglobulin G2 (IgG2), immunoglobulin G3 (IgG3) or immunoglobulin G4 (IgG4). In one embodiment, a nucleotide sequence encoding a fragment crystallizable region (Fc) of a human immunoglobulin G1 (IgG1) may be obtained from GenBank Accession number AF150959 which is a nucleotide sequence encoding a fragment crystallizable region (Fc) of a human immunoglobulin G1 (IgG1).

In one embodiment, the above-mentioned fusion protein is a bivalent.

Moreover, the amino acid sequence of the antibody of the present disclosure mentioned above may be a human sequence, and thus the fusion protein of the present disclosure is a fully human antibody. Since the fusion protein of the present disclosure is a fully human antibody, the problem resulting in human anti-mouse antibodies (HAMA) during the application of the antibody of the disclosure may be prevented.

In addition, the antibody may be connected to a labeling material and used as an imaging agent. Therefore, in a further embodiment of the present disclosure, the present disclosure may provide an imaging agent which may comprise the antibody of the present disclosure and a labeling material connected to the antibody of the present disclosure.

In one embodiment, the labeling material may comprise a carrier and a chromogenic substance or radioactive substance connected to a surface of the carrier. The carrier may comprise a microsphere, a liposome, a micelle, a bead, a nanoparticle, colloidal gold, etc., but is not limited thereto. A suitable chromogenic substance may comprise a fluorescent dye, a magnetic resonance imaging (MRI) reagent or an iodine-containing imaging agent for X-ray imaging and computed tomography (CT), etc., but is not limited thereto. Examples for the radioactive substance may comprise Yttrium-90 (Y-90), Indium-111 (In-111) and Iodine-131 (I-131), etc. In this embodiment, the labeling material may be a fluorescent particle.

In another embodiment, the labeling material itself is a chromogenic substance or radioactive substance. The chromogenic substance may comprise, but is not limited to, a fluorescent dye, a magnetic resonance imaging (MRI) reagent or an iodine-containing imaging agent for X-ray imaging and computed tomography (CT), etc. Examples for the radioactive substance may comprise Yttrium-90 (Y-90), Indium-111 (In-111) and Iodine-131 (I-131), etc.

In one embodiment, by binding to a human transferrin receptor expressed by a cell, the imaging regent of the present disclosure is able to be used in an imaging method, such as magnetic resonance imaging (MRI), positron emission tomography (PET), etc.

Furthermore, by the antibody in the imaging regent of the present disclosure binding to a human transferrin receptor expressed by a cell, the imaging reagent is capable of entering the cell through receptor-mediated endocytosis, and thus the imaging reagent is able to accumulate in the cell and has the effect of enhancing cell imaging accordingly. Moreover, it is known that various kinds of cancers will over express human transferrin receptor, and since the imaging reagent of the present disclosure is able to accumulate in a cell, the imaging reagent of the present disclosure is suitable for imaging or detecting early cancers or smaller tumors. The method for detecting a cancer cell by an anti-transferrin receptor antibody may be referred to, for example, the work of Freedman M et al., (Acad Radiol. 16(5):627-37, 2009), Högemann-Savellano D et al., (Neoplasia. 5(6): 495-506, 2003) and Pirollo K F et al. (Mol Imaging. 5(1):41-52, 2006). In one embodiment, a cancer or tumor which is suitable for being imaged by the imaging reagent of the present disclosure may comprise, but is not limited to brain cancer, leukaemia, prostate cancer, lung cancer or breast cancer, etc.

In addition, in a further embodiment of the present disclosure, the present disclosure may provide a method for labeling or imaging a cell or tissue. The method may comprise the following steps, but is not limited thereto.

First, an imaging reagent is provided. The imaging reagent may comprise the antibody of the present disclosure mentioned above and a labeling material connected to the antibody of the present disclosure.

Then, the imaging reagent contacted the imaging agent with a cell or tissue to be labeled or imaged, wherein the antibody of the imaging agent binds to a human transferrin receptor expressed by the cell or tissue to be labeled or imaged an cause the cell or tissue to be labeled or imaged is labeled or imaged, accordingly.

In one embodiment, the labeling material may comprise a carrier and a chromogenic substance or radioactive substance connected to a surface of the carrier. The carrier may comprise a liposome, a micelle, a bead, a nanoparticle, colloidal gold, etc., but it is not limited thereto. A Suitable chromogenic substance may comprise a fluorescent dye, a magnetic resonance imaging (MRI) reagent or an iodine-containing imaging agent for X-ray imaging and computed tomography (CT), but is not limited thereto. Examples for the radioactive substance may comprise Yttrium-90 (Y-90), Indium-111 (In-111) and Iodine-131 (I-131), etc. In this embodiment, the labeling material may be a fluorescent particle.

In another embodiment, the labeling material itself is a chromogenic substance or radioactive substance. The chromogenic substance may comprise, but is not limited to, a fluorescent dye, a magnetic resonance imaging (MRI) reagent or an iodine-containing imaging agent for X-ray imaging and computed tomography (CT), etc. Examples for the radioactive substance may comprise Yttrium-90 (Y-90), Indium-111 (In-111) and Iodine-131 (I-131), etc.

Furthermore, in one embodiment of the present disclosure, the present disclosure further provides a pharmaceutical composition which is able to be used for treating cancer. The pharmaceutical composition mentioned above may comprise an effective amount of an antibody comprising a heavy chain variable region, wherein an amino sequence of the heavy chain variable region comprises a sequence represented by SEQ ID NO.: 1 or SEQ ID NO.: 2, and the antibody is capable of specifically binding to a human transferrin receptor.

The pharmaceutical composition may be used for treating brain cancer, leukaemia, prostate cancer, lung cancer or breast cancer, etc., but it is not limited thereto.

In one embodiment, the pharmaceutical composition may further comprise a pharmaceutically acceptable carrier or salt.

The above-mentioned pharmaceutically acceptable carrier may comprise, but is not limited to, a solvent, a dispersion medium, a coating, an antibacterial and antifungal agent, or an isotonic and absorption delaying agent. The pharmaceutical composition can be formulated into dosage forms for different administration routes utilizing conventional methods.

The above-mentioned pharmaceutically acceptable salt may comprise, but is not limited to, inorganic cation salts including alkali metal salts such as sodium salt, potassium salt or amine salt, alkaline-earth metal salts such as magnesium salt or calcium salt, and salts containing bivalent or quadrivalent cation such as zinc salt, aluminum salt or zirconium salt. In addition, the pharmaceutically acceptable salt may also comprise organic salt including dicyclohexylamine salt, methyl-D-glucamine, and amino acid salt such as arginine, lysine, histidine, or glutamine.

The pharmaceutical composition may be administered orally, parentally by an inhalation spray or via an implanted reservoir. The parental method may comprise subcutaneous, intracutaneous, intravenous, intramuscular, intraarticular, intraarterial, intrasynovial, intrasternal, intrathecal, and intralesional, as well as infusion techniques.

An oral composition can comprise, but is not limited to, tablets, capsules, emulsions and aqueous suspensions, dispersions and solutions.

EXAMPLES

1. Material and Method

Reagent

Human Domain Antibody Library Kit (containing human single domain phage display library, helper phage KM13 and E. coli TG1 strain) were obtained from MRC Geneservice (cat. no. DAB 1000). Human transferrin receptor was obtained from SCIPAC Ltd., Becton Dickinson, UK. U87 and K562 cells were obtained from American Type Culture Collection (MD, USA). Mouse myeloma NS0 cells were obtained from European Collection of Animal Cell Cultures (Wiltshire, UK). AlamarBlue™ dye, RPMI 1640 and MEM media were purchased from Invitrogen. Chemically defined medium HyQ CDM4NS0 was purchased from Hyclone Laboratories (Logan, Utah, USA).

Cell Culture

Human erythroleukemia cell line K562 were cultured in RPMI 1640 growth media containing 10% fetal bovine serum, penicillin, and streptomycin. Human U87 astrocytoma cells were cultured in MEM growth media supplemented with 10% fetal bovine serum, penicillin, and streptomycin. All cells mentioned above were grown at 37□ in a 5% $CO_2$) incubator. Cells were passaged by trypsinization with a ratio of 1:10 twice a week.

Monoclonal Phage ELISA

In the last selection round, positive clones were identified from individual clones of a group of selected clones by ELISA. First, a 96 well plate (Nunc Maxisorb) was coated with human transferrin receptor (50 ng/well) at 4° Covernight, and then washed with PBS twice, and non specific protein binding sites on the plate were blocked with 5% MPBS (skimmed milk in PBS). After that, the monoclonal phage was added to each well after being proliferated, and the plate was allowed to stand at room temperature for 1 hour. Then, after the plate was washed with PBST 5 times, HRP-conjugated anti-M13 antibodies (1:5,000 diluted in 5% MPBS) were added to the plate, and the plate was allowed to stand at 37° C. for 1 hour. After the plate was washed with PBST three times, TMB substrate (US Biological) was added to the plate to perform a peroxidase reaction. After the addition of stop solution (1 M $H_2SO_4$), the absorbance was monitored at 450 nm. After being identified as a positive clone, phagmid was extracted from the phage and sequencing was performed to the gene of the antibody.

DNA Sequencing of Clones

Sequencing was performed with the LMB3 primer 5'-CAGGAAACAGCTATGAC-3' (SEQ ID NO.: 5).

Creation of $V_H$-Fc Fusion Protein Construction

A bivalent antibody format was designed to increase antigen-antibody binding affinity by fusing a nucleotide sequence of a fragment crystallizable region (Fc) with a nucleotide sequence of a heavy chain variable region ($V_H$). The coding region of $V_H$-Fc is composed of an N-terminal $V_H$ nucleotide sequence and a C-terminal human Fc gene, wherein Fc is derived from human IgG1 (Fc=hinge-$CH_2$—$CH_3$), and the gene sequence thereof is obtained from GenBank Accession number AF150959.

The anti-human transferrin receptor domain antibodies, $V_H$A3 (the sequence thereof is represented by SEQ ID NO.: 1) and $V_H$D4 (the sequence thereof is represented by SEQ ID NO.: 2) were used to create $V_H$-Fc fusions, respectively, and the experiment for selecting $V_H$A3 and $V_H$D4 is further described in the Example 1 below. To express $V_H$-Fc fusion in mammalian cells, the $V_H$-Fc fusion was sub-cloned into a pSecTag2 vector.

Preparation of $V_H$A3Fc- or $V_H$D4Fc-Coupled Fluorescent Beads

50 μl of yellow-green fluorescent beads (1 μm diameter, Molecular Probes) was well mixed with 250 μl of HEPES binding buffer (HBB; 20 mM HEPES buffer in water, pH 7.2) and centrifuged at 3,000 g for 20 minutes at 4° C. The resulting pellet was suspended in 100 μl HBB containing either 1% BSA (negative control) or 200 μg/ml of the foregoing antibody and mixed well. By being allowed to stand for 1 hour at 37□, absorption of protein to beads was facilitated. After that, the solution of beads coupled with protein was centrifuged as mentioned above and suspended in 1% BSA and allowed to stand at 37° C. for a further hour to block the non-specific protein binding sites. Finally, the treated beads were washed with 1 ml of HBB 3 times and the pellet was suspended in 1 ml of HBB containing 1% BSA. The beads after being coupled ($10^9$/ml) were stored in the dark at 4° C.

Cell Viability Assay

Cells ($3 \times 10^3$) were inoculated in a well containing 100 μl assay media (basal media plus 1% serum) in a 96 well plates in triplicate. After culturing the cells for 24 hours, 100 μl of antibody solutions diluted in assay media were added to each well. Cells were allowed to grow for 4-5 days and then AlamarBlue™ reagent (volume ratio of cell solution to reagent was 1:10; Biosource International) was added. Then fluorescence intensity was read using a Multi-Well Plate Reader which was set with an excitation wavelength at 544 nm and an emission wavelength at 590 nm. Cell growth condition was determined by fluorescence intensity and inhibition of cell growth was calculated according to the following formula:

$$\% \text{ inhibition} = 100 \times \frac{F_{control\ cells} - F_{antibody\ treated\ cells}}{F_{control\ cells}}$$

2. Example 1

Figure 1:
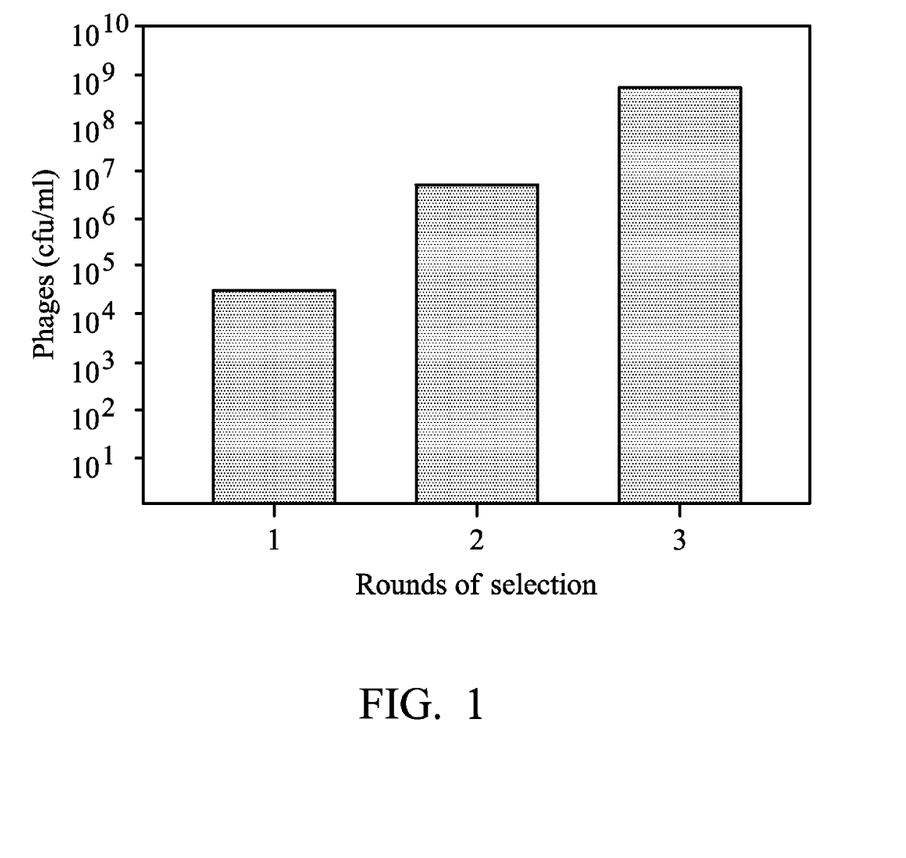
FIG. 1 shows the numbers (titer) for the phages after each round of selection in three rounds of selection according to one embodiment.

Selection of Human Transferrin Receptor From Human Single Domain
Phage Display Library by Phage Display Technique Phage display selections were performed using the immunotube (Maxisorp; Nunc, Roskilde, Denmark). Briefly, PBS containing 40 μg of human transferrin receptor was used to coat the tube at 4° C. overnight. The tube was washed with PBS three times and blocked with 5% MPBS (skimmed milk in PBS) at 4° C. overnight. Then, after the blocking solution was removed, the tube was washed with PBS three times. After that, $5 \times 10^{12}$ phages in 5% MPBS were added to the tube. After 1 hour of incubation at room temperature, the tube was washed with PBS-0.1% Tween-20 ten times and then washed with PBS twice. The phages bound to the human transferrin receptor in the tube were eluted by 1 mg/ml of trypsin (Sigma, cat. no. T1426), and amplification, PEG-precipitation and other rounds of panning were performed to the phages according to published protocols (Lee C M et al., Nat Protoc. 2(11):3001-8, 2007). After each round of panning was completed, the titer of the pages was monitored. The titers were $10^4$-$10^6$ cfu/ml after the first- and second-round selections. After three rounds of selection, titer of the phages were increased to $5 \times 10^8$ cfu/ml (see FIG. 1). Such an increase of titer of phages indicates the phages with human transferrin receptor single domain antibody were selected out. Then, 96 clones were randomly picked and identified as a positive clone or not by monoclonal phage ELISA. After that, two positive clones, $V_H A3$ and $V_H D4$ were sequenced, and the nucleotide sequences of heavy chain variable regions of $V_H A3$ and $V_H D4$ were determined as SEQ ID NO.: 3 and SEQ ID NO.: 4, respectively. The amino acid sequences of the heavy chain variable regions of $V_H A3$ and $V_H D4$ are predicted as SEQ ID NO.: 1 and SEQ ID NO.: 2, respectively.

3. Example 2

Production and Purification of Bivalent Anti-Human Tansferrin Receptor
Antibodies To increase avidity for human transferrin receptor, a nucleotide sequence of a fragment crystallizable region (Fc) and a nucleotide sequence of a heavy chain variable region ($V_H$) were fused in a manner of gene recombination to form a bivalent antibody format. The expression constructs of the recombinant gene was transfected into mouse myeloma NS0 cells using Effectene (Qiagen, Valencia, Calif., USA) according to the manufacturer's instructions and the transfected cells were cultured to make them express bivalent antibody. Stably expressive cell lines were cultured in a selection media containing 400 μg/ml Hygromycin B (Invitogen), a stable clone was cultured in HyQCDM4NS0 (Hyclone Laboratories) containing 2% fetal bovine serum in a shaker flask at an initial seeding density of $5 \times 10^5$ cells/ml. The $V_H$-Fc was purified from the culture media by protein A column (GE Healthcare). Purified bivalent antibodies were analyzed by 4-12% SDS-PAGE (Invitrogen) for evaluation of molecular weight and assessment of purity. Proteins in the gel were visualized by staining with Coomassie brilliant blue R-250. For western blot assay, proteins were transferred to nitrocellulose membrane from the gel. Next, the membrane was immersed in 5% MPBS for 1 hour for performing blocking and then the membrane was incubated with HRP-conjugated anti-human IgG Fc antibody (diluted in 5% MPBS by the ratio of 1:10,000) at room temperature for 1 hour. After that, the membrane was washed with PB ST. The luminescence signal was developed by the ECL western blotting reagent (Pierce) reacting with HRP on the membrane.

Figure 2A:
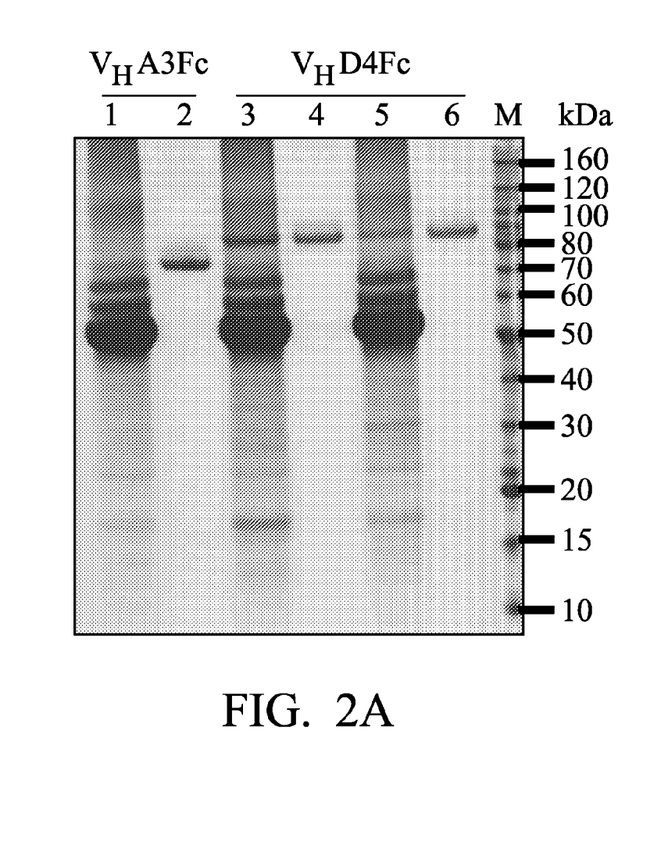
FIG. 2A shows results of SDS-PAGE analysis for purified $V_H$A3Fc antibody and $V_H$D4Fc antibody obtained form Example 2.
Figure 2B:
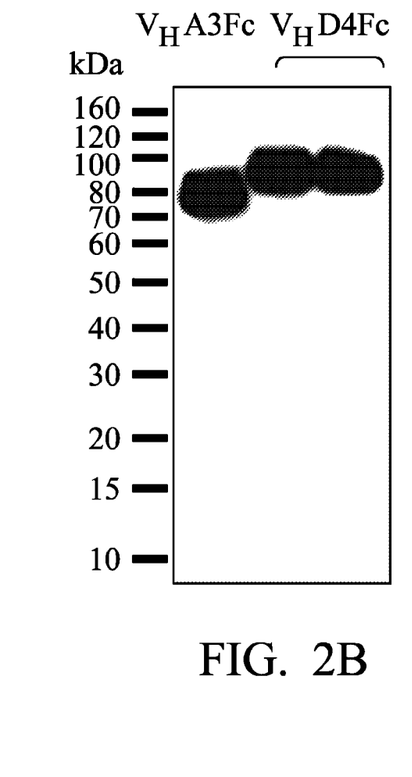
FIG. 2B shows results of western blot analysis for purified $V_H$A3Fc antibody and $V_H$D4Fc antibody obtained from Example 2.
Figure 2C:
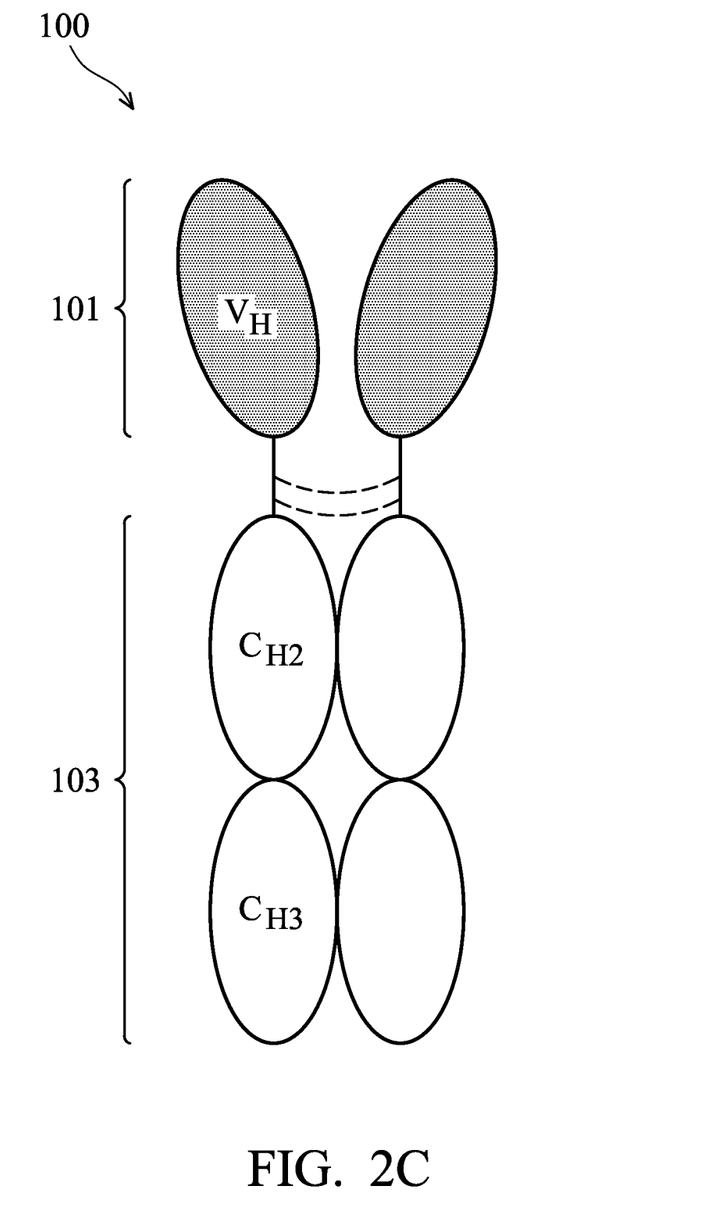
FIG. 2C shows a schematic diagram for a structure of a $V_H$-Fc bivalent antibody according to one embodiment.

Results of SDS-PAGE analysis and results of western blot of purified $V_H A3Fc$ antibody and $V_H D4Fc$ antibody were shown in FIG. 2A and FIG. 2B respectively. FIG. 2A and FIG. 2B clearly show that the purified $V_H A3Fc$ antibody and $V_H D4Fc$ antibody mainly correspond to their bivalent format. Moreover, FIG. 2C shows a schematic diagram for a structure of a $V_H$-Fc bivalent antibody.

4. Example 3

Binding Affinity of Bivalent Antibodies to Human Transferrin Receptor

After being purified, test of binding affinity to human tansferrin receptor was performed to the bivalent antibodies mentioned above. The binding affinities of bivalent antibody to the antigen were determined by ELISA. Briefly, 100 ng of human tansferrin receptor was added to a 96-well plate (Nunc Maxisorb plate) per well at 4° C., overnight. The plate was washed with PBS-0.05% Tween-20 three times and blocked with StartingBlock (Pierce) at 37° C. for 1 hour. Then, the plate was washed with PBST three times after the blocking solution was removed. The bivalent antibodies with different concentrations were added to each well, respectively, and the plate was allowed to stand at 37° C. for 1 hour. After three times of PBST washing, HRP-conjugated anti-human IgG Fc antibody (diluted in StartingBlock at a ratio of 1:10,000) was added to the 96 well, and the plate was incubated at 37° C. for 1 hour. After three times of PBST washing, TMB substrate (US Biological) was added to each well to perform a peroxidase reaction. After the addition of stop solution (1 M $H_2SO_4$), the absorbance was monitored at 450 nm. Then the equilibrium constant ($K_D$) for the antibody was calculated by the absorbance for antibodies with different concentrations.

Figure 3:
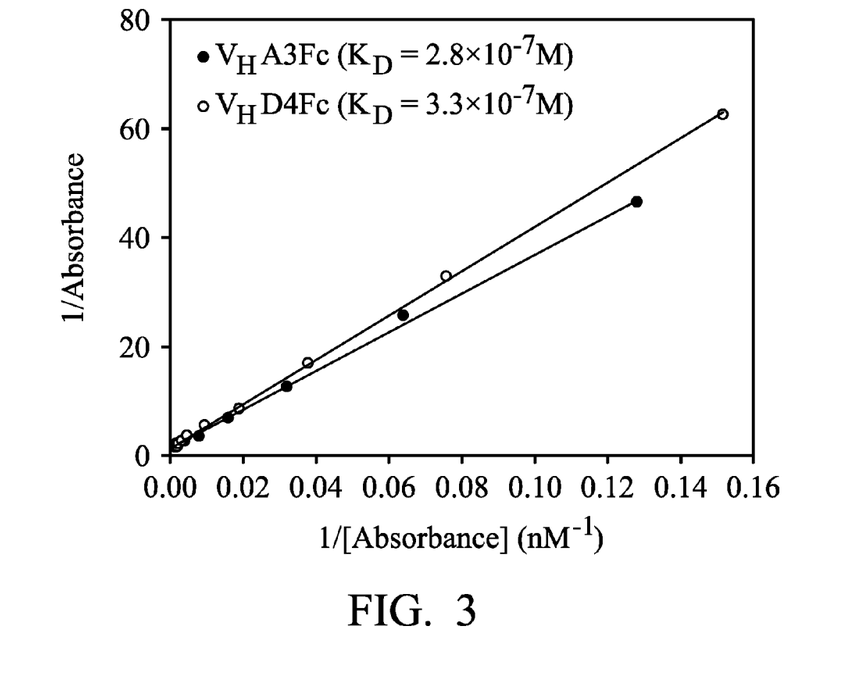
FIG. 3 shows the binding affinities of $V_H$A3Fc antibody and $V_H$D4Fc antibody obtained from Example 2 to human transferrin receptor.

FIG. 3 shows the binding affinities of $V_H A3Fc$ antibody and $V_H D4Fc$ antibody to human transferrin receptor. According to FIG. 3, it is known that the equilibrium constant ($K_D$) values of $V_H A3Fc$ antibody and $V_H D4Fc$ antibody to human transferrin receptor were approximately $2.8 \times 10^{-7}$ M and $3.3 \times 10^{-7}$ M, respectively.

5. Example 4

Internalization Assays With $V_H A3Fc$- or $V_H D4Fc$-Coupled Fluorescent Beads

To determine whether bivalent antibodies were internalized through human transferrin receptor on cell surface, antibody-coupled fluorescent beads and K562 cells (highly expressed human transferrin receptors) were used to perform the test. K562 cells ($1 \times 10^6$) were suspended into 400 μl of RPMI 1640 serum-free media (SFM) containing 0.1% BSA. In either the presence or the absence of sodium azide, after equilibrium at 37° C. for 5 minutes, 100 μl of treated beads (prepared as describe earlier) were added to the tubes with a final ratio of cells to beads at approximately 1:100, and the tube allowed to stand at 4° C. or 37° C. for 1 hour. Cells in the tube were washed with cold PBS three times to remove unbound beads and were fixed by Cytofix Fixation Buffer. Sodium azide, an inhibitor for internalization, was used as a control and the BSA-coupled fluorescent beads were used as a negative control. Fluorescence was measured by FACS. The results are shown in Table 1 and FIG. 4.

TABLE 1

Fluorescence intensity in cells determined from K562 cells treated with fluorescent beads coupled with different antibodies (proteins)

| Treatment | Mean fluorescence intensity (MFI) | | |
|---|---|---|---|
| | $V_HA3Fc$ | $V_HD4Fc$ | BSA |
| 4° C. | 5.92 | 3.63 | 1.45 |
| 37° C. | 228.15 | 71.77 | 9.07 |
| 37° C., Na-azide | 70.62 | 24.38 | 3.49 |

Figure 4:
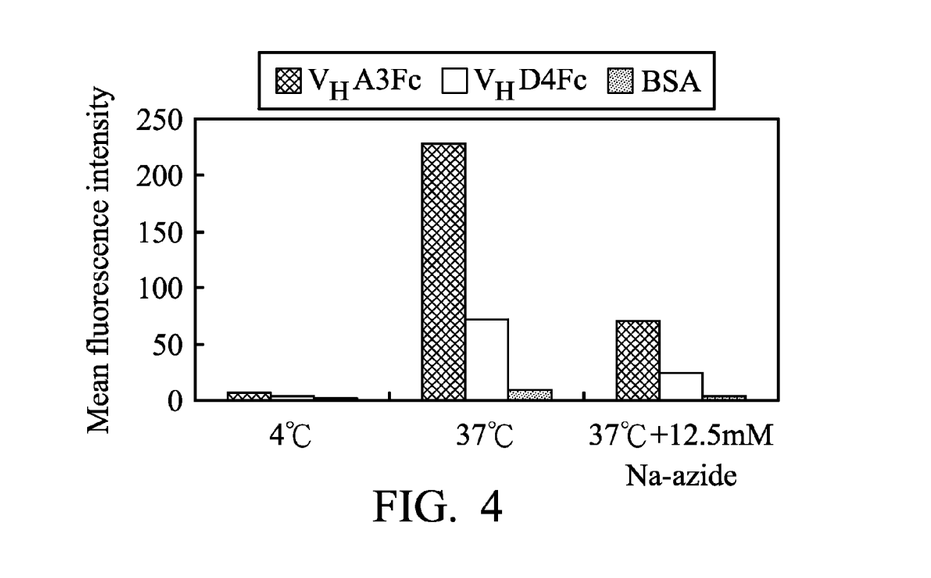
FIG. 4 shows the results of internalization assays for $V_H$A3Fc antibody or $V_H$D4Fc antibody-coupled fluorescent beads at different temperatures, wherein $V_H$A3Fc antibody and $V_H$D4Fc antibody were obtained from Example 2.

Table 1 and FIG. 4 show that at 37° C. and in the absence of sodium azide, fluorescent beads coupled with $V_HA3Fc$ or $V_HD4Fc$ were capable of binding to human transferrin receptor and mediated by human transferrin receptor to enter cells through endocytosis to cause the mean fluorescence intensity of the cells to be higher than those for negative control and control. Accordingly, it is confirmed that $V_HA3Fc$ or $V_HD4Fc$ is capable of binding to the human transferrin receptor and entering cells through receptor-mediated endocytosis.

Moreover, bivalent antibodies to transferrin receptor may be used to detect the presence or absence of cancerous cells in a variety of tissues because overexpression of endogenous transferrin receptor has been described for various malignant cells. Transferrin receptor may represent a potential molecular imaging label to increase detection of smaller tumors. Such diagnostic methods have been reported by Freedman M et al., (Acad Radiol. 16(5):627-37, 2009), Högemann-Savellano D et al., (Neoplasia. 5(6): 495-506, 2003) and Pirollo K F et al. (Mol Imaging. 5(1):41-52, 2006). By linking the antibody to a radioactive or MRI contrast agent, the radioactive or MRI contrast agent is capable of entering a cell through receptor-mediated endocytosis and accumulating in the cell, and allowing imaging machinery to visually identify the location of the labeled antibody binding to the antigen expressed on the surface of cancer cells, imaging diagnosis for tumor location is achieved. Therefore, $V_HA3Fc$- or $V_HD4Fc$-coupled MRI contrast agent may become a potential tool in imaging tumors.

6. Example 5

Bivalent Antibodies Inhibit Cancer Cells Growth

Figure 5A:
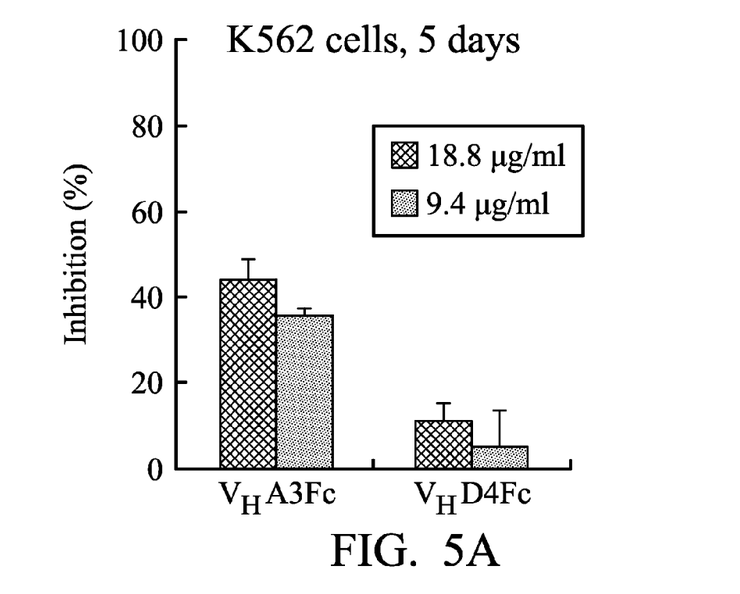
FIG. 5A shows inhibition rates for K526 cells treated with $V_H$A3Fc antibody or $V_H$D4Fc antibody obtained from Example 2 for 5 days.
Figure 5B:
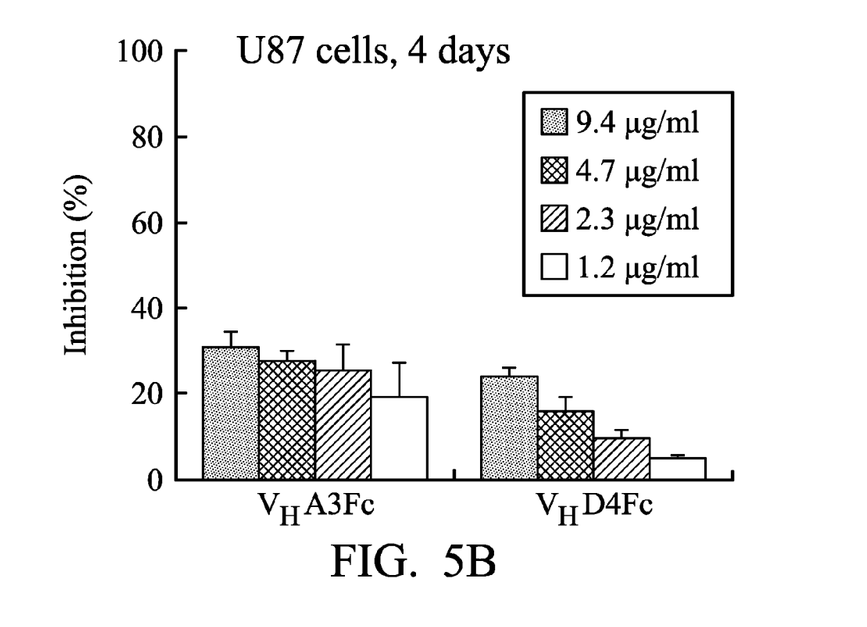
FIG. 5B shows inhibition rates for U87 cells treated with $V_H$A3Fc antibody or $V_H$D4Fc antibody obtained from Example 2 for 4 days.

To test the effect of bivalent antibodies on K562 and U87 cell lines, cells were cultured in medium containing antibodies with various concentrations for 4-5 days. Cell viability was estimated by AlamarBlue™ staining as described earlier. The results are shown in FIG. 5A and FIG. 5B. FIG. 5A shows that $V_HA3Fc$ effectively inhibits the growth of K562 and U87 cell lines. For $V_HA3Fc$, the greatest inhibition of the cell growth for K562 cell lines was determined as 45% inhibition.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. An isolated anti-human transferrin receptor antibody, comprising:
   a heavy chain variable region of which the amino acid sequence is represented by SEQ ID NO.: 1 or SEQ ID NO.: 2,
   wherein the anti-human transferrin receptor antibody is capable of specifically binding to a human transferrin receptor.

2. The isolated anti-human transferrin receptor antibody as claimed in claim 1, wherein the amino sequence of the heavy chain variable region represented by SEQ ID NO.: 1 is encoded by a nucleotide sequence represented by SEQ ID NO.: 3.

3. The isolated anti-human transferrin receptor antibody as claimed in claim 1, wherein the amino sequence of the heavy chain variable region represented by SEQ ID NO.: 2 is encoded by a nucleotide sequence represented by SEQ ID NO.: 4.

4. The isolated anti-human transferrin receptor antibody as claimed in claim 1, wherein the anti-human transferrin receptor antibody is capable of entering a cell through receptor-mediated endocytosis.

5. A fusion protein, comprising:
   the isolated anti-human transferrin receptor antibody as claimed in claim 1; and
   a fragment crystallizable region (Fc) of a human immunoglobulin G connected to the anti-human transferrin receptor antibody,
   wherein the fusion protein is capable of specifically binding to a human transferrin receptor.

6. The fusion protein as claimed in claim 5, wherein the fusion protein is bivalent.

7. The fusion protein as claimed in claim 5, wherein the fusion protein is capable of entering a cell through receptor-mediated endocytosis.

8. An imaging agent, comprising:
   the isolated anti-human transferrin receptor antibody as claimed in claim 1; and
   a labeling material connected to the anti-human transferrin receptor antibody.

9. The imaging agent as claimed in claim 8, wherein the labeling material comprises:
   a carrier; and
   a chromogenic substance or radioactive substance connected to a surface of the carrier.

10. The imaging agent as claimed in claim 9, wherein the carrier comprises a liposome, a micelle, a bead, a nanoparticle or colloidal gold.

11. The imaging agent as claimed in claim 9, wherein the chromogenic substance comprises a fluorescent dye, a magnetic resonance imaging (MRI) reagent or an iodine-containing imaging agent for X-ray imaging and computed tomography (CT).

12. The imaging agent as claimed in claim 9, wherein the radioactive substance comprises Yttrium-90 (Y-90), Indium-111 (In-111) or Iodine-131 (I-131).

13. The imaging agent as claimed in claim 8, wherein the labeling material is a chromogenic substance or radioactive substance.

14. The imaging agent as claimed in claim 13, wherein the chromogenic substance comprises a fluorescent dye, a magnetic resonance imaging (MRI) reagent or an iodine-containing imaging agent for X-ray imaging and computed tomography (CT).

15. The imaging agent as claimed in claim 13, wherein the radioactive substance comprises Yttrium-90, Indium-111 or Iodine-131.

16. A method for labeling or imaging a cell or tissue, comprising:
   providing an imaging agent, wherein the imaging agent comprises the isolated anti-human transferrin receptor antibody as claimed in claim 1 and a labeling material connected to the anti-human transferrin receptor antibody; and
   contacting the imaging agent with a cell or tissue to be labeled or imaged, wherein the antibody of the imaging agent binds to a human transferrin receptor expressed by the cell or tissue and causes the cell or tissue be labeled or imaged.

17. A pharmaceutical composition, comprising:
   an effective amount of an isolated antibody comprising a heavy chain variable region, wherein an amino sequence of the heavy chain variable region comprises a sequence represented by SEQ ID NO.: 1 or SEQ ID NO.: 2, and the antibody is capable of specifically binding to a human transferrin receptor.

18. The pharmaceutical composition as claimed in claim 17, wherein the pharmaceutical composition is used for a treatment of brain cancer, leukaemia, prostate cancer, lung cancer or breast cancer.

* * * * *